United States Patent [19]

Hussain et al.

[11] Patent Number: 5,753,701
[45] Date of Patent: May 19, 1998

[54] N-CHLORO-N-METHYL GLUCAMINE AND N-CHLORO-N-METHYL GLUCAMINE ESTERS AS NOVEL SAFE AGENTS FOR WATER DISINFECTION

[75] Inventors: Anwar A. Hussain; Bassam Tashtoush; Lewis W. Dittert, all of Lexington, Ky.

[73] Assignee: University of Kentucky, Lexington, Ky.

[21] Appl. No.: 736,913

[22] Filed: Oct. 25, 1996

[51] Int. Cl.⁶ ............... C07C 219/06; A01N 37/04
[52] U.S. Cl. ............... 514/547; 514/669; 560/252; 564/507; 424/169; 424/185
[58] Field of Search ............... 514/669, 546, 514/547; 564/507; 424/1.69, 1.85; 560/252

[56] References Cited

U.S. PATENT DOCUMENTS

| Re. 29,903 | 2/1979 | Kirby et al. | 514/669 |
|---|---|---|---|
| 2,463,885 | 3/1949 | Kuehl, Jr. et al. | 514/669 |
| 2,538,106 | 1/1951 | Kuehl, Jr. et al. | 514/669 |
| 2,802,819 | 8/1957 | Lederer et al. | 514/669 |
| 2,884,411 | 4/1959 | Heyns | 514/669 |
| 2,918,462 | 12/1959 | Druey et al. | 514/669 |
| 2,922,783 | 1/1960 | Kuhn et al. | 514/669 |
| 3,987,029 | 10/1976 | Kirby et al. | 514/669 |
| 4,071,560 | 1/1978 | Kirby et al. | 514/669 |
| 4,375,542 | 3/1983 | Waitz et al. | 514/669 |
| 4,377,583 | 3/1983 | Larsen et al. | 514/669 |
| 4,386,103 | 5/1983 | Pogany et al. | 514/669 |
| 5,424,402 | 6/1995 | Hussain et al. | 514/669 |
| 5,449,770 | 9/1995 | Shumate et al. | 514/669 |

OTHER PUBLICATIONS

Hussain et al., "Chloramine–T in Radiolabeling Techniques" *Analytical Biochemistry* (1995) 224:221–226.

Hussain et al., "Chloramine–T in Radiolabeling Techniques" *Analytical Biochemistry* (1993) 214:495–499.

Seevers et al., "Radioiodination Techniques for Small Organic Molecules" *Chem. Rev.*(1982) 82:575–590.

*Primary Examiner*—Robert Gerstl
*Attorney, Agent, or Firm*—Burns, Doane, Swecker & Mathis, L.L.P.

[57] ABSTRACT

The present invention relates to N-chloro-N-methyl glucamine and N-chloro-N-methyl glucamine esters, and their use as agents for water disinfection and as mild oxidizing agents for the radiolabeling of oxidation-sensitive biomolecules.

14 Claims, 7 Drawing Sheets

N-CHLORO-N-METHYL GLUCAMINE AND N-CHLORO-N-METHYL GLUCAMINE ESTERS AS NOVEL SAFE AGENTS FOR WATER DISINFECTION

BACKGROUND OF THE INVENTION

1. Field of the Invention

The present invention relates to N-chloro-N-methyl glucamine and N-chloro-N-methyl glucamine esters, and their use as agents for water disinfection and as mild oxidizing agents for the radiolabeling of oxidation-sensitive organic molecules.

2. Description of the Related Art

Chloramines are widely known as useful water disinfecting agents. Among the most popular chloramine water disinfecting agents is halazone (p-N,N-dichlorosulfamylbenzoic acid). While effective, halazone suffers from some important disadvantages, including its strong, unpleasant chlorine odor, its sensitivity to light, its relatively low solubility in water, and, perhaps most importantly, the formation of potentially carcinogenic chlorinated hydrocarbons which are generated as the result reaction with impurities commonly found in water supplies. In view of these disadvantages, it should be apparent that there still exists a need in the art for improved water disinfecting agents.

Chloramines, in particular chloramine-T (CAT) are frequently used in the radiolabeling of organic molecules by halogenation, for example, as described in U.S. Pat. No. 5,424,402 ("the '402 patent"), the contents of which are incorporated herein by reference. According to the method of the '402 patent an organic molecule may be radiolabeled by reaction with $^{125}I_2$. Normally, the $^{125}I_2$ is released from its sodium salt by oxidation with chloramine-T. The disadvantage of this procedure is that residual CAT in the reaction mixture frequently causes oxidative decomposition of the organic molecule rendering the procedure useless. There exists a need for a mild oxidizing agent that is capable of releasing molecular halogens from their salts without oxidizing organic molecules to be labeled.

N-methyl glucamine is known in the prior art as a solubilizing agent in the formulation of intravenous pharmaceuticals, enabling high concentrations of pharmaceuticals to be administered. However, prior to the present invention the particular substituted glucamines of the present invention, and their use in the purification of water, was not known.

SUMMARY OF THE INVENTION

Accordingly, a major object of the present invention is to meet the art-recognized need for a safe, effective and inexpensive method for disinfection of water supplies. Advantageously, the compounds of the present invention minimize the formation of the carcinogenic chlorinated hydrocarbons which are currently generated as the result of disinfection with halazone and similar agents. Furthermore, these compounds satisfy the need for an agent that can be conveniently used in households to disinfect water, especially in developing nations, as a replacement for Halazone.

The present inventors have found that chlorination of N-methyl glucamine yields N-chloro-N-methyl glucamine, a powerful germicidal agent. The compounds of the present invention have the following structure:

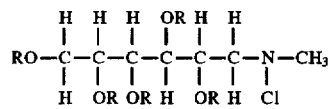

wherein R is —H or —COR$_2$, wherein R$_2$ is lower alkyl. These compounds are useful as disinfecting agents, particularly for disinfecting water supplies. When used as a disinfectant, the compounds of the present invention generate N-methyl glucamine, a very safe agent, in parts per millions.

A further object of the present invention is to meet the need for a mild oxidizing agent for use in radiohalogenation procedures involving oxidation-sensitive organic molecules and similar substrates. The present inventors have observed that the N-chloro derivatives of secondary amines, such as N-methyl glucamine and its esters, are much weaker oxidizing agents than N-chloro compounds, such as chloramine-T and halazone. When used in radiohalogenation procedures, N-chloro secondary amines do not oxidize most organic molecules.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

Figure 1:
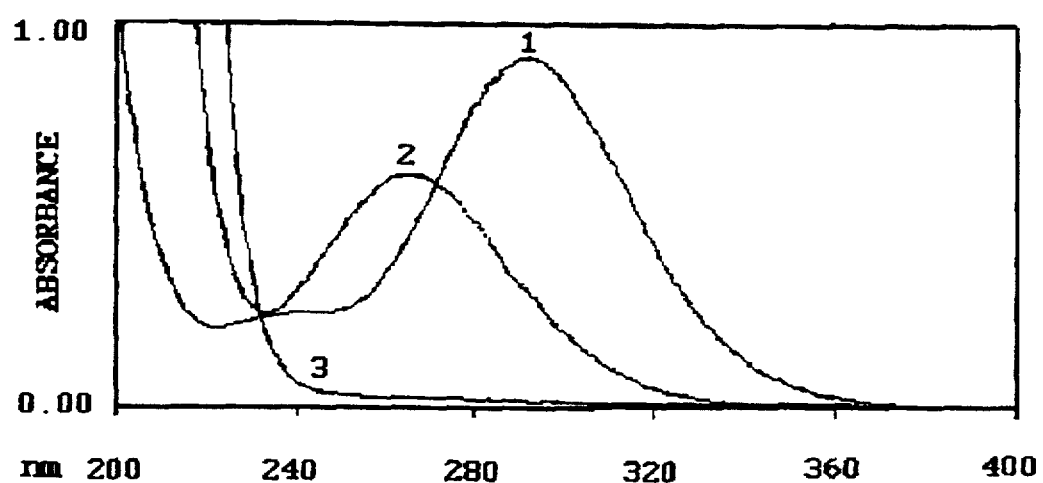
FIG. 1: UV absorbance spectra of NaOCl (1), penta-O-acetyl-N-chloro-N-methylglucamine (NCMG)(2), and penta-O-acetyl-N-methylglucamine (NMG)(3).

The present inventors have found that chlorination of N-methyl glucamine yields N-chloro-N-methyl glucamine, a powerful germicidal agent. The compounds of the present invention comprise the following structure:

larly for disinfecting water supplies. When used as a disinfectant, the compounds of the present invention generate N-methyl glucamine, a very safe agent, in parts per millions.

The compounds of the present invention are also useful as mild oxidizing agents for use in radiohalogenation procedures involving oxidation-sensitive organic molecules, in particular oxidation-sensitive biomolecules and similar substrates. The present inventors have observed that the N-chloro derivatives of secondary amines, such as N-methyl glucamine and its esters, are much weaker oxidizing agents than N-chloro compounds, such as chloramine-T and halazone. When used in radiohalogenation procedures, N-chloro secondary amines do not oxidize most biomolecules.

The compounds of the present invention may be synthesized by any means known to the skilled artisan. Preferably, the compounds of the present invention are prepared from N-methylglucamine, which may be obtained commercially or may be synthesized according to any method known to the skilled artisan. For example, N-methylglucamine may be synthesizes from D-glucose and methylamine according to the method of Karrer (*Helv. Chim. Acta* 20:83 (1937), the contents of which are incorporated herein by reference).

The present invention also provides compositions of matter comprising one or more of the compounds of the present invention and a suitable carrier therefor. These compositions may also include other disinfectant compounds, including chlorinating compounds such as halazone, or other antibiotic agents. Compositions according to the present invention may be formulated in any manner suitable for use as a disinfectant. For example, compositions of the present invention may be provided as aqueous solutions or suspensions. More preferably, the compositions of the present invention are provided in solid form. Particularly preferred are tablet and granular forms of the composition of the present invention, which provide for easy storage and handling. Tablets and granules may be formulated according to any means known in the art. For the purposes of the present invention tablets may be of any convenient size; granules are small grains of the composition of the present invention; preferably, said grains are between two and four millimeters in diameter.

The present invention also provides a method of disinfecting water comprising adding the compounds or compositions of the present invention in an amount sufficient to disinfect the water. For the purposes of the present invention, disinfection encompasses killing bacteria and protozoans living in the water to be disinfected. Preferably, the compounds or compositions of the present invention will be added to the water to be disinfected such that the final concentration of the compounds of the present invention in the water will be at least 10 parts per million (ppm), more preferably from 60–200 ppm, most preferably 105 ppm.

The present invention also provides a method for non-destructively radiolabeling biomolecules by halogenation. The method of the present invention is advantageously applied to radiolabeling of oxidation-sensitive organic molecules, particularly oxidation-sensitive biomolecules. The method of the present invention comprises (a) reacting a compound according to the present invention with a radiolabeled halide salt and an organic molecule which is desired to be radiolabeled such that said radiolabeled halogen reacts directly with said organic molecule to produce a radiohalogenated organic molecule; and (b) recovering said radiohalogenated organic molecule. The method of the present invention may advantageously be carried out in the presence of a buffer. In a preferred embodiment, the method of the present invention provides that the compound according to the present invention and the radiolabeled halide salt are mixed together first, such that the radiolabeled halide salt is converted into molecular radiolabeled halogen; then, the organic compound to be labeled is added to the mixture.

For use in the present invention, the radiolabeled halogen salt is preferably selected from the group consisting of sodium, potassium, lithium, rubidium, cesium, magnesium, calcium, and ammonium salts. Particularly preferred are sodium halogen salts, most preferably sodium iodide.

The following examples are presented in order to more fully illustrate the preferred embodiments of the invention. They should in no way be construed, however, as limiting the broad scope of the invention.

EXAMPLE 1

Preparation of Penta-O-Acetyl-N-Chloro-N-Methylglucamine (NCMGE)

a. Synthesis of Penta-O-Acetyl-N-Methylglucamine (NMGE)

Penta-O-Acetyl-N-Methylglucamine Perchlorate

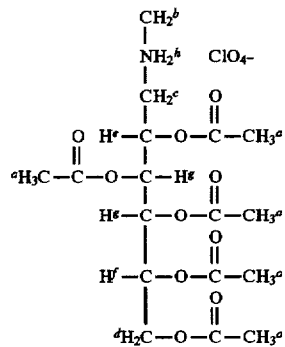

N-methylglucamine(10 g) was dissolved in 7.4 g (4.4 ml) of (70%) perchloric acid in a round bottom flask. Ethyl acetate (500 ml) was added. The solution was stirred, and 73 g of acetyl chloride was added dropwise. The solution was left stirring at room temperature for four days until a white solid was formed. The resulting white solid was filtered and washed with ether and recrystallized from acetone/petroleum ether mixture and dried overnight in a vacuum oven. The melting point of the solid was 148°–150° C.; MW 504.45; $^1$H-NMR (DMSO-d$_6$) (FIG. 1): δ 2.05 (15H, m, protons a), 2.56 (3H, S, protons b), 3.13 (2H, m, protons c), 4.20 (2H, m, protons d), 4.98 (1H, proton e), 5.05 (1H, m, proton f, 5.27 (2H, protons g), 8.47 (2H, broad s, protons h).

b. Synthesis of Penta-O-Acetyl-N-Chloro-N-Methylglucamine (NCMGE)

Penta-O-Acetyl-N-Chloro-N-Methylglucamine

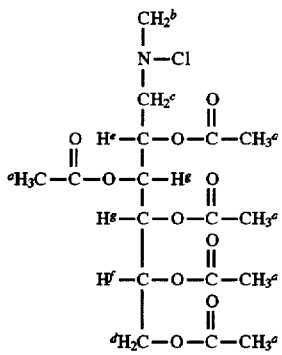

Penta-O-acetyl-N-methylglucamine (3.0 g) was dissolved in water and the pH of the solution was adjusted 6.0 by addition of 2N NaOH solution. Chlorine gas was bubbled into the solution for a few minutes until a white solid was formed. The solid was filtered and washed with water and dried in a vacuum oven. The melting point was 77°–79° C.; MW 439.45; $^1$H-NMR (CDCl$_3$): δ 2.08 (15H, m, protons a), 2.93 (3H, S, protons b), 3.05 (2H, m, protons c), 4.20 (2H, m, protons d), 5.10 (IH, proton e), 5.40 (IH, m, proton f), 5.44 (2H, protons g).

Elemental analysis: Found: C,46.24; H, 5.9 1; N, 3.17; Cl, 8.15%.

Calculated for $C_{17}H_{26}O_{10}NCl$: C, 46.41; H, 5.9 1; N, 3.18; Cl, 8.08%.

The product was also identified by UV spectrophotometry (FIG. 1).

EXAMPLE 2

The Use of NCMGE in Radiolabeling Techniques

1. Chemical Stability of a Model Amino Acid (1-Aminocyclo-hexane Carboxylic Acid) in the Presence of Chloramine-T, NCMG, and NCMGE N-chloro amino acids, such as N-chloro-1-aminocyclohexane carboxylic acid, which are formed by chlorination of the amine group, are very unstable (Hussain et al. 1995 *Analyt. Biochem* 224:221–226; Awad et al. 1990 *J. Pharm Sci.* 79:1121–1122; the contents of both of these articles are incorporated herein by reference). Their decompositions are associated with loss of chlorine titer. In order to determine whether NCMG and NCMGE chlorinate 1-aminocyclohexanecarboxylic acid, iodometric titration was used to follow the reaction.

A solution of 1-aminocyclohexanecarboxylic acid containing 2×10$^{-3}$M was prepared in 0.1M phosphate buffer (pH 7.0) and equilibrated for 2 minutes at 25° C. For the Chloramine-T (CAT) experiments, a solution of CAT (1×10$^-$ 3M) in water was freshly prepared and equilibrated for 2 minutes at 25° C. Equal volumes (10.0 ml) of the two solutions were mixed (t=0) and stored at 25° C. Aliquots of the mixture (4.0 ml) were assayed periodically using standard iodometric titration; i.e. addition of excess KI and back titration of the liberated iodine with sodium thiosulfate using starch as an indicator. A control experiment was carried out by following the chlorine titer of a solution of CAT in phosphate buffer in the absence of the amino acid.

For the experiments with NCMG and NCMGE, a solution of either NCMG or NCMGE (1×10$^{-3}$M) in phosphate buffer (0.1M, pH 7.0) was freshly prepared and equilibrated for 2 minutes at 25° C., and a 10.0 ml aliquot was mixed with an equal volume of 1-aminocyclohexanecarboxylic acid (0.02M), (t=0). The mixture was stored at 25° C. and assayed periodically by titration, as described above. A control experiment was conducted in the absence of the amino acid.

2. Iodination of L-tyrosine

Solutions

Phosphate buffer (0.01M, pH 7.4): A total of 5.0 g of NaCl, 0.1 g KCl, 0.57 g Na$_2$HPO$_4$, and 0.1 g KH$_2$PO$_4$ were dissolved in 500 ml of glass distilled water. The pH of the solution was adjusted to 7.4 with either NaOH or HCl, as needed.

L-tyrosine solution: A total of 25 mg of L-tyrosine was dissolved in 100 ml of phosphate buffer.

Sodium Iodide solution: A total of 207 mg of sodium iodide was dissolved in 100 ml phosphate buffer.

Penta-O-acetyl-N-chloro-N-methylglucamine solution (NCMGE): A total of 141 mg of NCMGE was dissolved in 100 ml of phosphate buffer (0.01M, pH 7.4).

Experimental

The HPLC system for analysis was as follows:

Mobile phase=Distilled water/methanol/85% phosphoric acid=(550/450/8).

Flow rate=1.0 ml/min.

Detector UV wavelength 254 nm

Temperature=ambient.

Method I: A total of 0.2 ml of L-tyrosine solution, 0.02 ml sodium iodide solution, and 0.108 ml of phosphate buffer were mixed in a tube for two minutes, then 0.172 ml of NCMGE solution was added (t=0), and 50 µl samples were withdrawn at 2 and 15 minutes and injected directly into the HPLC.

Method II: A total of 0.2 ml of L-tyrosine solution, and 0.02 ml of sodium iodide solution were mixed in a tube for 2 minutes, then 0.780 ml of NCMGE solution was added, and 50 µl samples were withdrawn at 2 and 15 minutes and injected directly into the HPLC.

3. Iodination of leucine enkephalin

Solutions

Phosphate buffer (0.01M, pH 7.4), sodium iodide solution, and NCMGE solution were the same as those for the iodination of tyrosine.

Leucine enkephalin solution: A total of 8.9 mg of leucine enkephalin was dissolved in 10 ml of phosphate buffer (0.01M, pH 7.4).

Experimental

The HPLC system for analysis was described above (Section 2). The conditions were the same as those described above for the analysis of iodinated tyrosine products, except the mobile phase was (0.1M NaH$_2$PO$_4$/Methanol=1/1) and the detector UV wavelength was set at 270 nm.

Method I: A total of 0.2 ml of leucine enkephalin, 0.020 ml sodium iodide solution, and 0.083 ml of phosphate buffer were mixed in a tube for 2 minutes, then 0.172 ml of NCMGE solution was added (t=0). At the end of the reaction (2 and 15 minutes), 25 pl of 20% sodium thiosulfate solution was added and 50 µl samples were withdrawn and injected directly into the HPLC. The addition of sodium thiosulfate was found necessary to decompose the residual NCMGE because NCMGE interfered with the enkephalin peaks in the HPLC.

Method II: A total of 0.2 ml of leucine enkephalin and 0.020 ml sodium iodide were mixed in a tube for 2 minutes and NCMGE solution (0.755 ml) was added (t=0). At the end of the reaction (2 and 15 minutes), 25 µl of 20% sodium thiosulfate solution was added and 50 µl samples were withdrawn and injected directly into the HPLC.

4. Iodination of L-tyrosine

Figure 2:
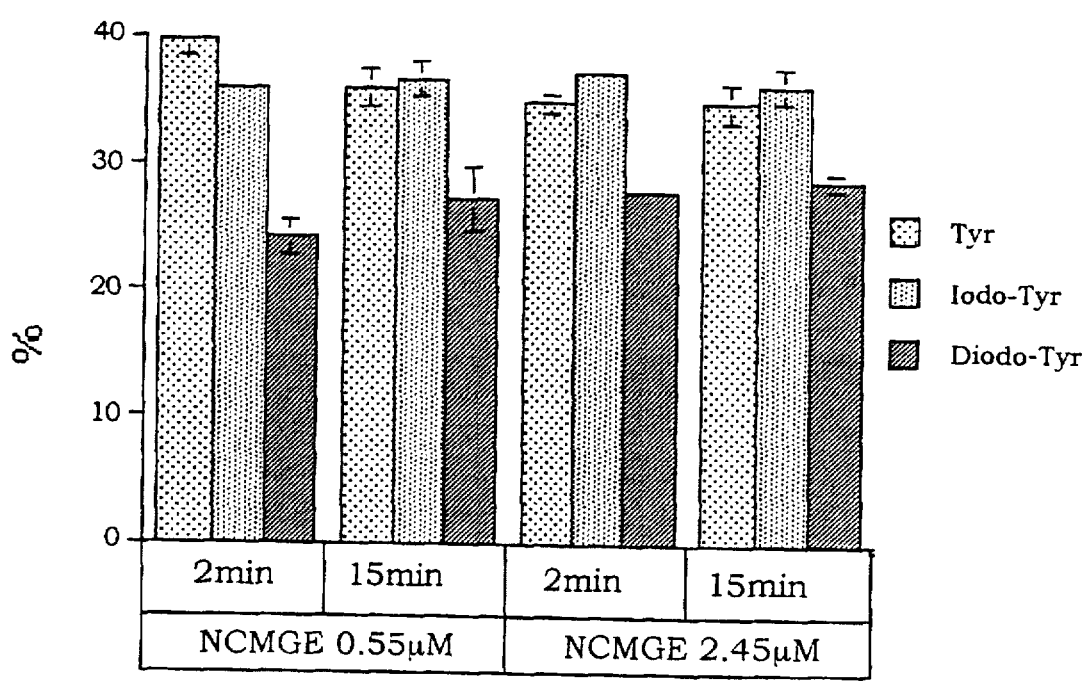
FIG. 2: Fraction of L-tyrosine (Tyr), mono-3-iodo-L-tyrosine (Iodo-Tyr), and 3,5-diiodo-L-tyrosine (Diiodo-Tyr) for four methods of iodinating L-tyrosine in phosphate buffer (0.01M, pH 7.2).

To determine whether NCMGE would have practical activity in the radiohalogenation of amino acid, L-tyrosine, was selected as a model and compared with the method employed by Hussain et. al (1995 Analyt. Biochem 224:221–226), the contents of which are incorporated herein by reference. The results in FIG. 2 show that when NCMGE was used, the yield of the two iodinated species of L-tyrosine were significantly greater with both 2 and 15 minutes incubation times than those obtained with CAT and iodobead and close to that of N-chloromorpholine.

5. Iodination of leucine enkephalin

Figure 3:
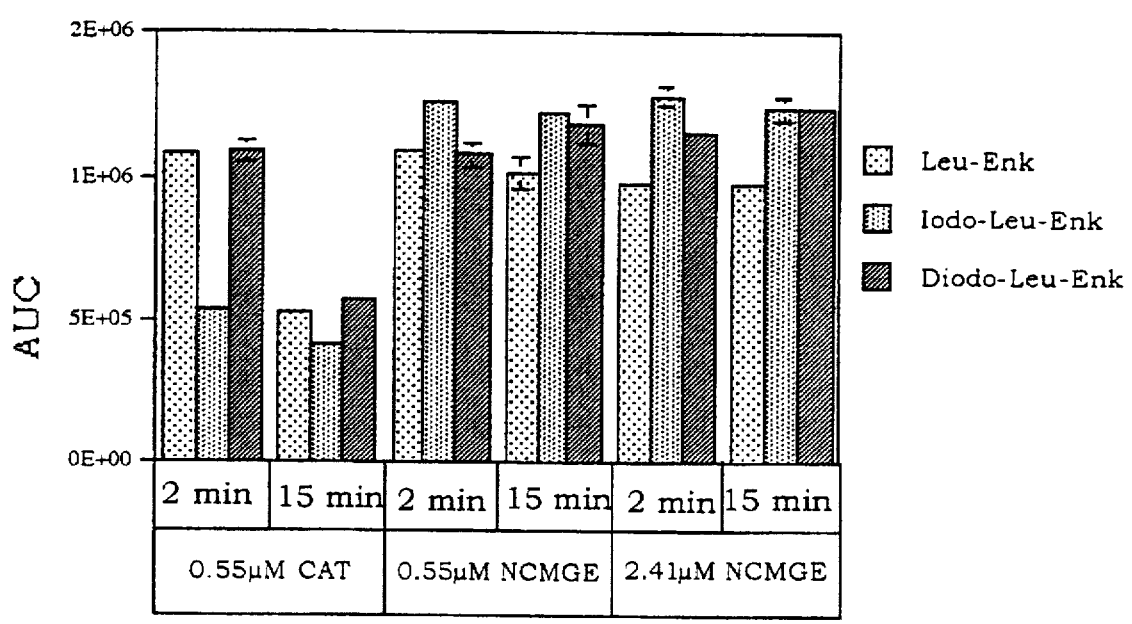
FIG. 3: Peak areas of leucine enkephalin (Leu-Enk), iodoleucine enkephalin Iodo-Leu-Lek), and diiodoleucine enkephalin (Diiodo-Leu-Enk) for six methods of iodinated leucine enkephalin in phosphate buffer.

To determine whether NCMGE would have practical utility in radiohalogenation of small peptide, leucine enkephalin was selected as a model substrate for comparison of iodination procedures employing CAT solution and NCMGE. The methods were tested using 2 and 15 minute incubation times. The results in FIG. 3 show that when NCMGE was used, the yield of the two iodinated leucine enkephalin species were significantly greater with both 2 and 15 minutes incubation times. When CAT was used alone with a 15 minutes incubation time, the yield of the apparent diiodinated species (labeled diiodo leu-enk in FIG. 3) was significantly smaller than when NCMGE was present. This appears to be the result of decomposition of leucine enkephalin, as indicated by the smaller amount of all species following 15 minutes exposure to CAT alone (see FIG. 3).

EXAMPLE 3

The germicidal activity of Penta-O-acetyl-N-chloro-N-methylglucamine (NCMGE)

The antimicrobial activity of NCMGE was examined in the following experiments:

A. *Legionella pneumophila*

*Legionella pneumophila* strain AA100 was inoculated into buffered charcoal-yeast extract (BCYE) agar plates and incubated for 48 hours at 37° C. The bacteria were suspended into 0.01M phosphate buffer pH 7.4 to an optical density of 0.7–0.8 at 550 nm.

15 µl of bacterial suspension was mixed with 7.0 ml 0.01M phosphate buffer (pH 7.4) containing disinfectant compounds as listed in Table I. The concentration of bacteria in this suspension was approximately 1 million bacteria/ml. After 30 minutes the activity of the disinfectant compounds was quenched with 0.4 ml 0.01M sodium bisulfite.

TABLE 1

| Names and concentrations of N-chloro compounds used in germicidal experiment. | |
|---|---|
| Compound | Concentration |
| Control | 0 |
| Monochloramine (NH$_2$Cl) | 10 |
| Penta-O-acetyl-N-chloro-N-methylglucamine | 30 |
| Penta-O-acetyl-N-chloro-N-methylglucamine | 60 |
| Penta-O-acetyl-N-chloro-N-methylglucamine | 105 |

Two aliquots of 20 µl of the final solution of each of the above was diluted in 0.01M phosphate buffer to approximate bacterial concentrations of $10^3$ and $10^2/100$ µl. 100 µl of the two final dilutions were grown on BCYE agar plates that were incubated at 37° C. for three days. At the end of the three day incubation period, the colony forming unit was enumerated. Another experiment was conducted against the serogroups of *Legionella pneumophila* using NCMGE in a concentration of 105 ppm.

B. Coincubation of *Hartimannella vermiformis* and *Legionella pneumophila*

Amoebae *H. vermiformis* were suspended in assay medium to give a final concentration of $10^5$ cell per ml. Tissue culture flasks containing amoebae were inoculated with *Legionella pneumophila*, suspended in Pucks' saline to give a final concentration of $10^3$ bacteria per ml, and incubated at 37° C. 1.2 ml aliquots were withdrawn immediately and 1, 2, 3, 5, and 7 days after inoculation. Of the 1.2 ml, 0.2 ml was cultured on BCYE agar plates in order to follow the increase in the number of bacteria. The remaining 1.0 ml was centrifuged at 8000 rpm for 5 minutes. The bacterial pellet was washed twice with sterile deionized water. The pellet was then suspended in 1.0 ml 105 ppm NCMGE solution for 30 minutes. After 30 minutes, two 20 µl aliquots of this NCMGE solution were diluted in 0.01M phosphate buffer to an approximate bacterial concentration of $10^3$ and $10^2/100$ µl. 100 µl of these two dilutions were deposited on BCYE agar plates and incubated at 37° C. for three days. At the end of the three day period, the colony forming units were enumerated.

Results

Figure 4:
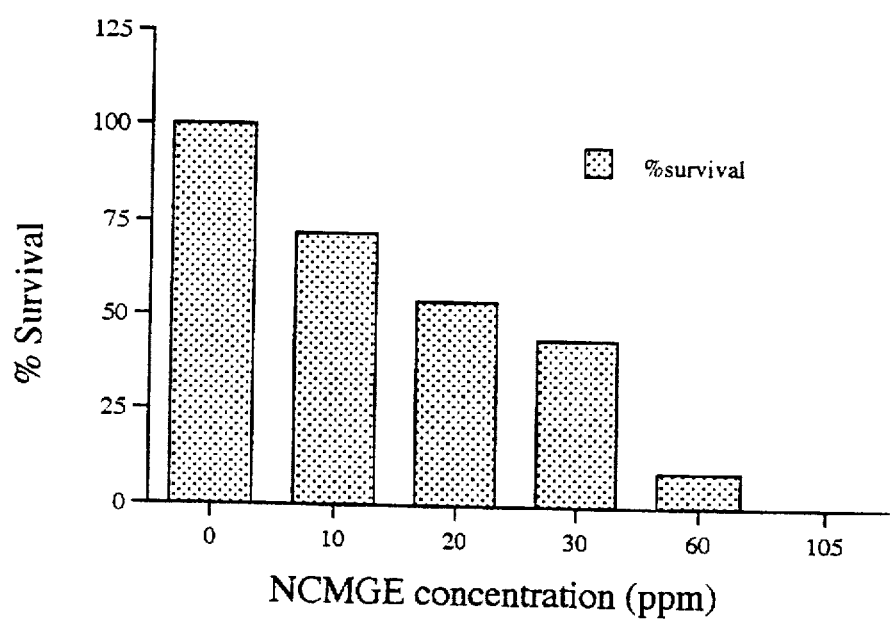
FIG. 4: Susceptibility of L. pneumophila AA100 to different NCMGE concentrations.
Figure 5:
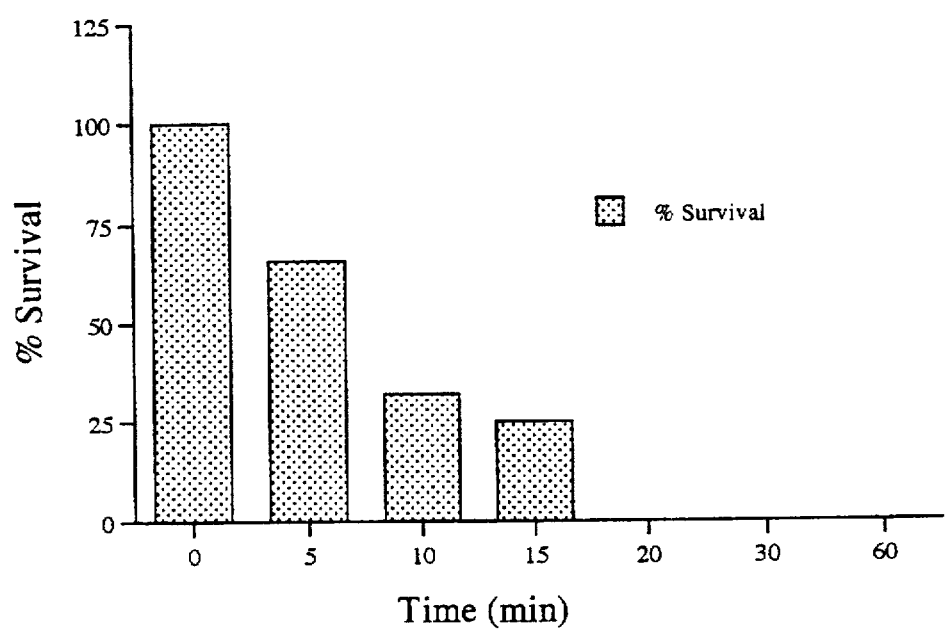
FIG. 5: Kinetics of killing of L. pneumophila by 105 ppm NCMGE.

The antimicrobial activity of N-chloramine penta-O-acetyl-N-chloro-N-methylglucamine (NCMGE) was examined against *Legionella pneumophila* first using the minimum inhibitory concentration (MIC) method. This method is based on incubation of the organism for 30 minutes at different NCMGE concentrations. The results shown in FIG. 4 indicate that the MIC for NCMGE is 105 ppm. Second the antimicrobial activity was examined using the contact germicidal efficiency (CGE). This method involves examining the bactericidal activity of NCMGE (105 ppm) at different incubation times. After each time interval, the chlorine activity of NCMGE was quenched by 0.01M sodium bisulfite. The results in FIG. 5 indicate that the shortest time for which growth of *L. pneumophila* is not observed was found to be 20 minutes.

The antimicrobial activity of NCMGE (105 ppm) was also examined against a serogroups of *L. pneumophila* compared to a control of 1000 cfu and incubation time of 30 minutes. The results shown in Table II show that this NCMGE concentration kills all the strains of Legionella to which it was exposed.

TABLE II

Susceptibility of *L. pneumophila* serogroups to 105 ppm NCMGE compared to a control of 1000 cfu and incubation time of 30 minutes.

| Serogroup | Strain | % Survival |
|---|---|---|
| 1* | Philadelphia 1 | 0 |
| 2 | Togus 1 | 0 |
| 3 | Bloomington 2 | 0 |
| 4 | Los Angeles 1 | 0 |
| 5 | Dallas 1 | 0 |
| 6 | Chicago 2 | 0 |
| 7 | Chicago 8 | 0 |
| 8 | Concord 3 | 0 |
| 9 | IN 23 | 0 |
| 10 | Leiden 1 | 0 |
| 11 | 797-PA-H | 0 |
| 12 | 570-Co-H | 0 |
| 13 | 82A3105 | 0 |

*The serogroups of *L. pneumophila* are distinguished by their lipopolysaccharide antigen.

Figure 6:
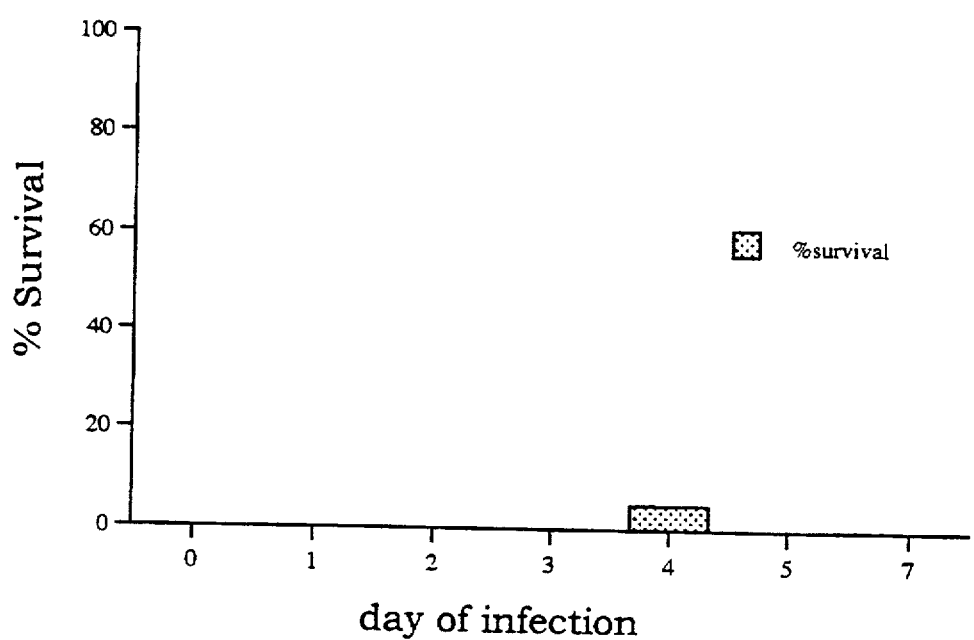
FIG. 6: Susceptibility of L. pneumophila AA100 in co-culture with H. vermiformis to 105 ppm NCMGE in 30 minutes incubation.
Figure 7:
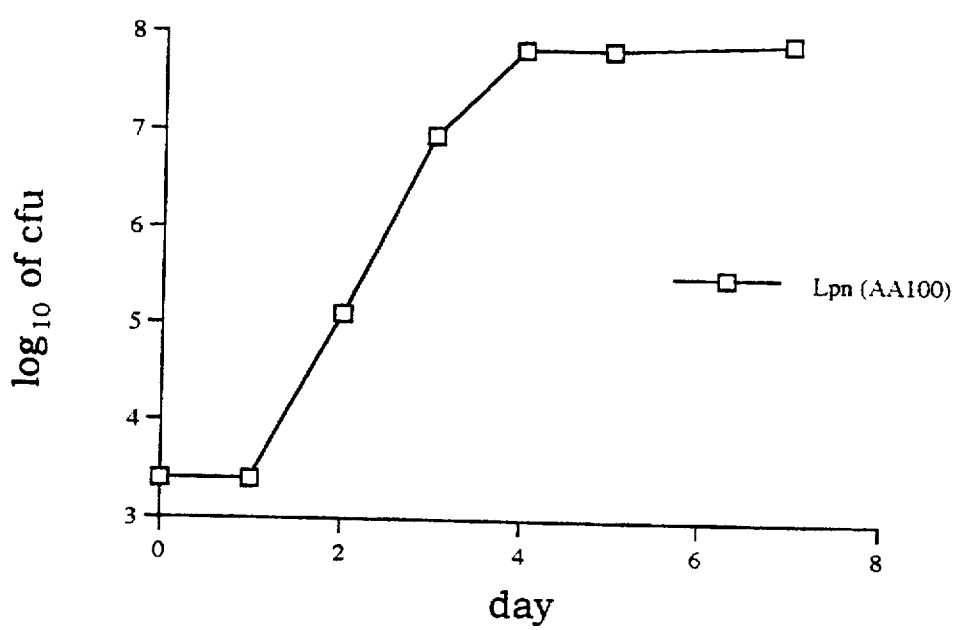
FIG. 7. Kinetics of multiplication of L. pneumophila AA100 within H. vermiformis.

Finally, the antimicrobial activity of NCMGE (105 ppm) was tested against a coculture of *Legionella pneumophila* and *H. vermiformis* in which the *L.pneumophila* typically become more resistant to chlorine. The results shown that NCMGE (105 ppm) killed 95% of the bacteria at day 4 (FIG. 6), the time at which *L. pneumophila* typically reach their maximum growth (as shown in FIG. 7). The results in FIG. 6 also demonstrate that NCMGE has a powerful sustained antimicrobial activity.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A substituted N-chloro-N-methyl glucamine compound comprising the following structure:

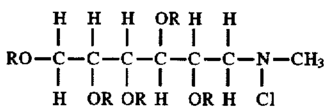

wherein R is —H or —$COR_2$, wherein $R_2$ is lower alkyl.

2. The compound of claim 1, wherein $R_2$ is methyl.

3. The compound of claim 1, wherein $R_2$ is ethyl.

4. The compound of claim 1, wherein said compound is penta-O-acetyl-N-chloro-N-methylglucamine.

5. A composition of matter comprising one or more compounds according to claim 1, and a carrier therefor.

6. The composition of claim 5, wherein said composition is formulated as a solid.

7. The composition of claim 6, wherein said solid composition is formulated as granules.

8. The composition of claim 6, wherein said composition is formulated as tablets.

9. The composition of claim 5, wherein said composition is formulated as an aqueous solution of one or more compounds according to claim 1.

10. A method of disinfecting water comprising adding to water to be disinfected one or more compounds according to claim 1 in an amount sufficient to kill bacteria and protozoans in the water.

11. The method of claim 10, wherein the compound or compounds are added in an amount sufficient to kill all the bacteria and protozoans in the water.

12. The method of claim 10, wherein the final concentration of the compounds of the present invention in the water is at least 10 parts per million (ppm).

13. The method of claim 10, wherein the final concentration of the compounds of the present invention in the water is from 60–200 ppm.

14. The method of claim 10, wherein the final concentration of the compounds of the present invention in the water is 105 ppm.

* * * * *